Figure 1:
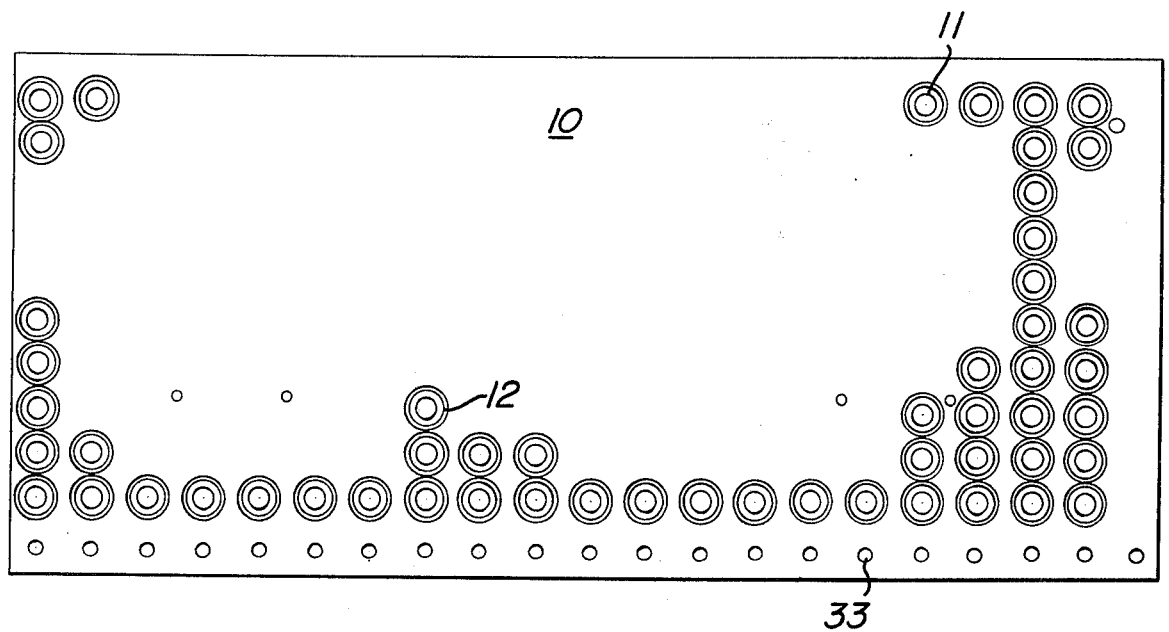

United States Patent [19]
Johnson, Jr. et al.

[11] 4,011,048
[45] Mar. 8, 1977

[54] INCUBATION APPARATUS

[75] Inventors: Edgar G. Johnson, Jr.; Howard L. McGill, both of Huntsville, Ala.

[73] Assignee: Micromedic Systems, Inc., Horsham, Pa.

[22] Filed: June 17, 1976

[21] Appl. No.: 697,172

[52] U.S. Cl. .............................. 23/259; 23/253 R
[51] Int. Cl.[2] ..................... G01N 33/16; B01L 7/00
[58] Field of Search ............ 23/230 R, 230 B, 259, 23/292, 253; 195/127, 139; 119/36

[56] References Cited
UNITED STATES PATENTS

| | | | |
|---|---|---|---|
| 3,556,731 | 1/1971 | Martin | 23/259 X |
| 3,634,651 | 1/1972 | Siegel et al. | 23/259 X |
| 3,790,346 | 2/1974 | Ritchie | 23/253 R |

*Primary Examiner*—R.E. Serwin

[57] ABSTRACT

An incubation apparatus for use in automated biochemical analyzer systems which comprises a block of thermoconductive material having rows of wells for the reception of sample carriers to be incubated with temperature control attached to the block; the block resting with well openings facing downward upon a pair of insulating plates so arranged that by movement of one of the plates, a row of wells is exposed so as to allow a number of sample carriers, equivalent in number to the number of wells in a row, to be loaded into that row of wells, the sample carriers being in alignment with and directly below the row of wells; and a means for lifting the sample carriers up into the wells or lowering sample carriers down out of the wells.

8 Claims, 7 Drawing Figures

INCUBATION APPARATUS

This invention relates to incubators for use in biochemical analyzer systems and, more particularly, for use in such systems that are essentially entirely automated.

Increasing sophistication of various analytical devices has given rise to the automation of many of the individual steps to be performed in these devices. Thus, it is desirable to have a device which, once loaded with a great number of samples to be analyzed, can be activated to perform all the necessary steps leading up to display of analysis results without need for intervening manual operations by an operator of the device. Such a device is needed in biochemical analyzer systems, where it is often necessary for the operator to perform various manual operations during the course of a complete analysis. One such very common operation is an incubation step. In many analytical biochemical procedures, it is necessary to incubate samples for a period of time in order to bring about some biochemical process prior to sending the samples to the actual analyzing step.

In many conventional analytical devices, incubators, whether of the bath type or of the dry bath or heat block type, must be manually loaded. The problems with the former type are loss of water due to evaporation, rusting, messiness, long warmup time, excessive power consumption if left on constantly to overcome the long warmup time, and the like. The heat block type, however, overcomes these disadvantages, while having the major disadvantages that test tubes have to be manually inserted and removed, increasing the likelihood of identifaction error, while consuming excessive time, as well as often not being able to accept entire racks of test tubes.

The present invention has not only overcome the disadvantages of the heat block type incubator design, but has also fully automated the operations of loading, incubating and unloading sample carriers.

The incubation apparatus of the present invention comprises
- a block of thermoconductive material having means for temperature control attached thereto and a plurality of rows of regularly spaced wells, said wells extending into the block from a bottom surface of the block and having openings facing downward;
- a pair of flat plates of insulating material, said plates lying in the same plane, each with an edge in mutual abutment, one plate being fixed and the other longitudinally slidable a given incremental distance in a direction away from the point of abutment, with the block with well openings facing downward being slidably carried upon said pair of insulating plates; and
- means for lifting into a row of wells a set of sample carriers from a carrier holder disposed directly beneath and in alignment with said row of wells in the block, and for lowering a set of sample carriers from a row of wells into a carrier holder disposed directly beneath and in alignment with the row of wells.

As will be hereinafter disclosed, by proper activation of control switches, the insulating plates are parted by an incremental distance, exposing a row of wells into which are loaded sample carriers by the lifting means, the block being partially or completely sequentially loaded, with the plates then closing so as to completely contain the loaded sample carriers in the incubation block. The carriers can likewise be unloaded by reversing the loading procedure.

Figure 2:
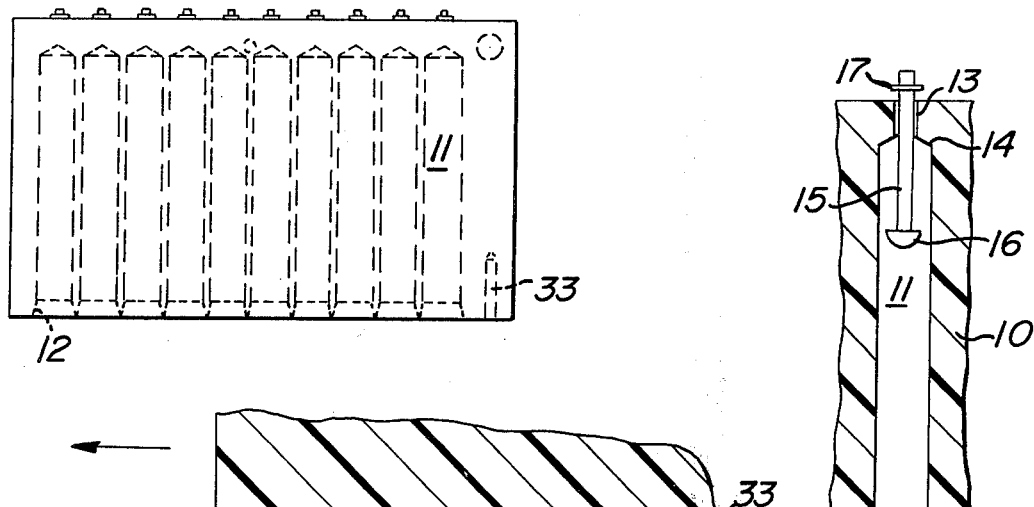
Figure 3:
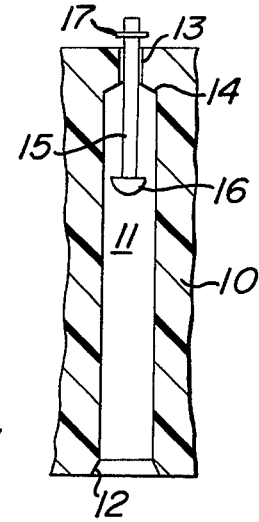
Figure 7:
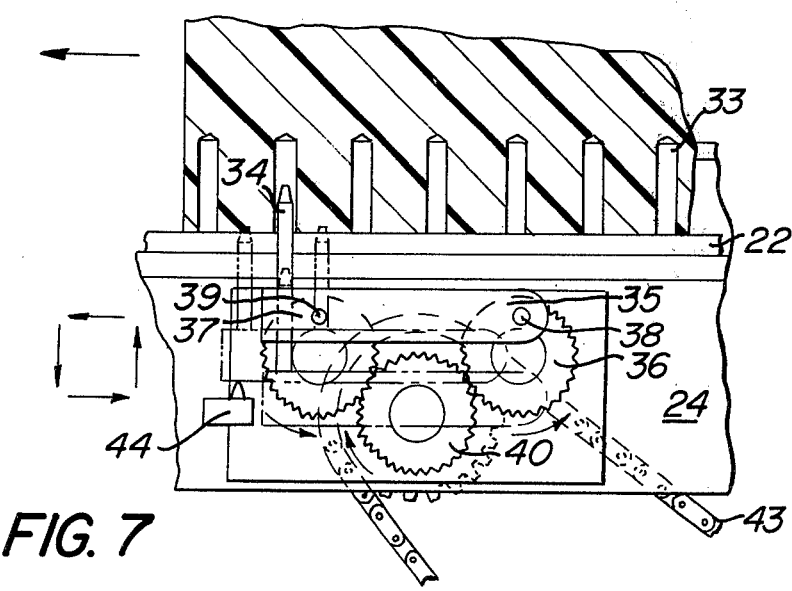
Figure 4:
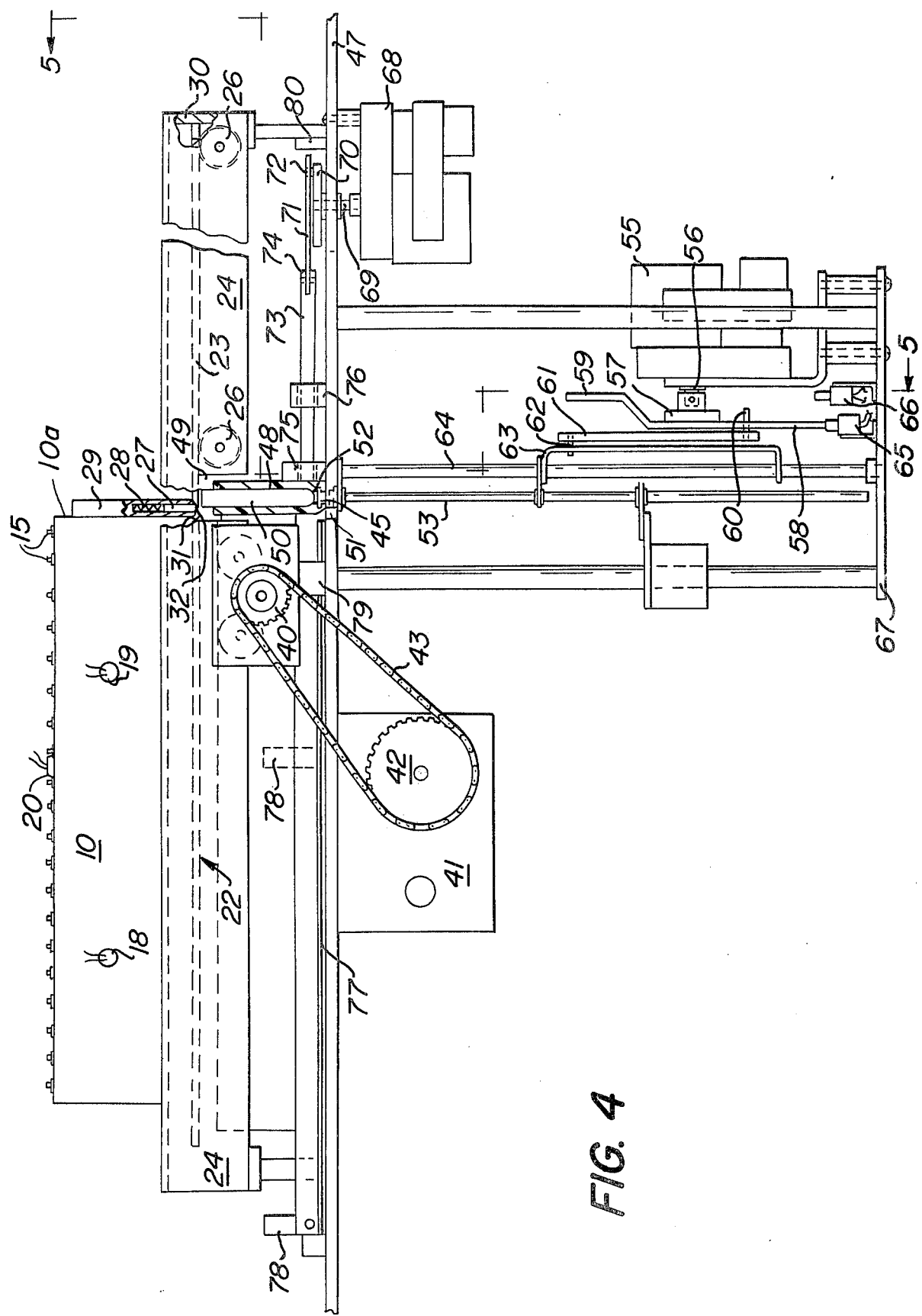
Figure 5:
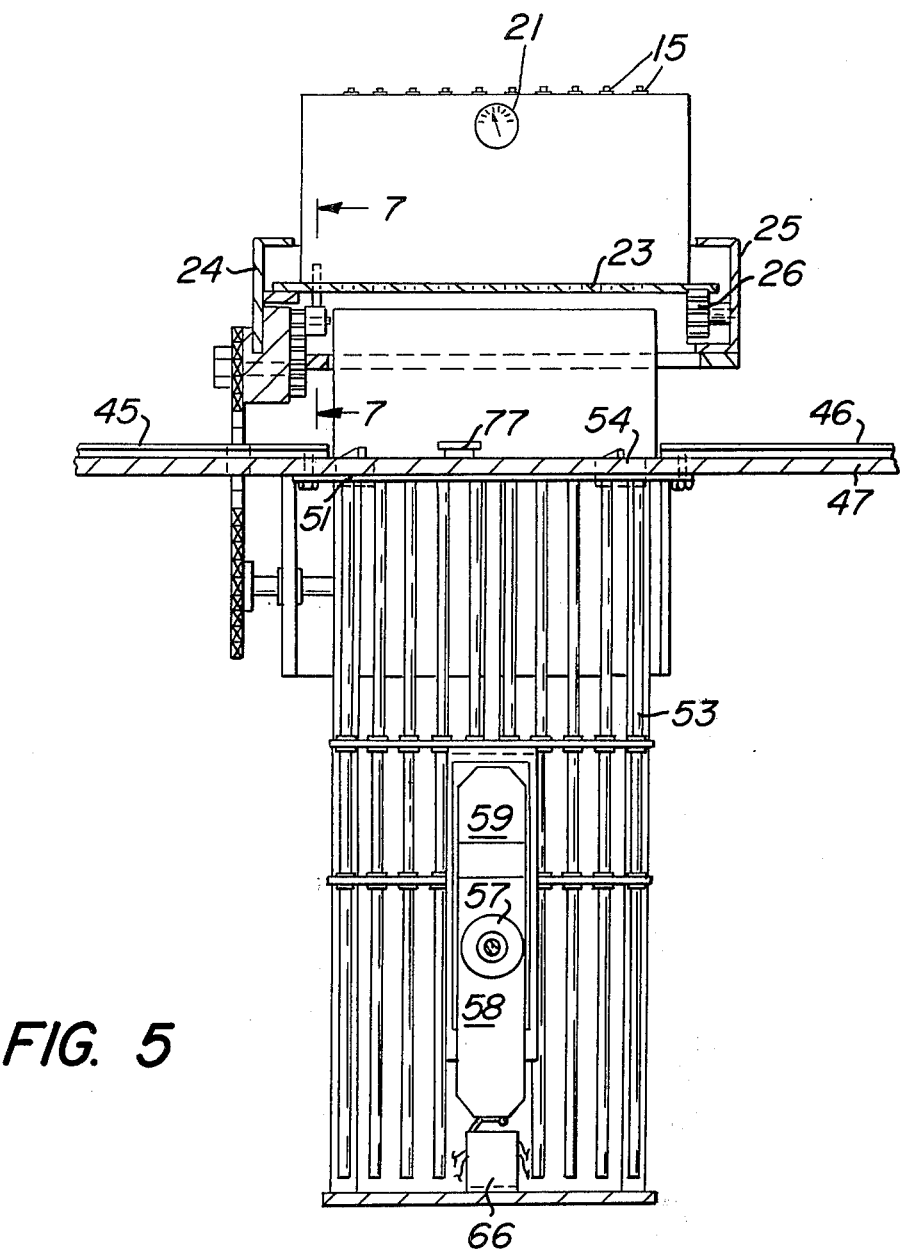
Figure 6:
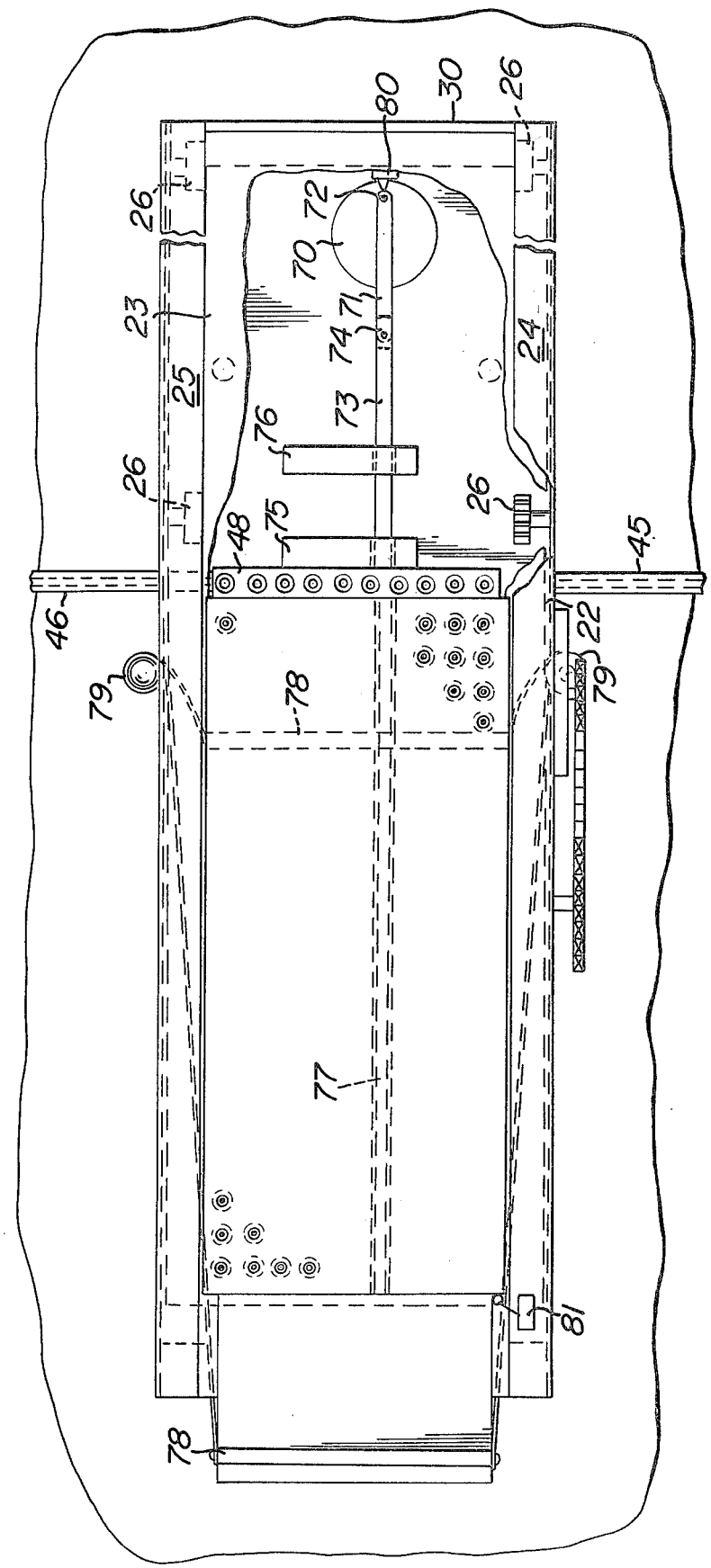

The various advantages and features of the present invention can be appreciated more fully hereinafter from a consideration of the detailed description which follows, taken together with the accompanying drawings, wherein one embodiment of the invention is illustrated by way of example, in which:

FIG. 1 - is a bottom plan view of the incubator block;

FIG. 2 - is an end view of the incubator block;

FIG. 3 - is a detailed fragmentary cross-sectional view of a well in the block;

FIG. 4 - is a cross-sectional side elevational view of the complete apparatus;

FIG. 5 - is a sectional view of the apparatus shown in FIG. 4 taken along line 5—5 in FIG. 4;

FIG. 6 - is a top view of the incubation apparatus;

FIG. 7 - is a detail view of the indexer device taken along line 7—7 in FIG. 5.

Referring now to the drawings, in FIG. 1, a block 10 of thermoconductive material, preferably a metal and most preferably aluminum, is provided with regularly spaced rows of wells 11 formed therein. The numbers and spacing of the wells in the rows and of the rows in the block are a matter of design and requirement considerations. In the embodiment shown, the block has twenty rows of wells, with ten wells per row. As seen in FIG. 2, the wells extend into the block from the bottom surface of the block to a point just short of the top surface of the block. This is designed so that sample carriers to be incubated will be contained completely within the well. In order to facilitate the entry of sample carriers, such as open-ended test tubes, into the wells, the well openings are countersunk to give the opening a flare 12. Likewise, to prevent sample carriers from hanging up in the wells and to thereby effectuate their expulsion, each well 11 is provided with a means for aiding in the expulsion, such as shown in FIG. 3. Through an opening 13 in each well extremity 14, the opening passing completely through the block, extends a rod 15 of suitable length, at one end of which is formed or attached a weight 16, while on that portion of the rod projecting beyond the block 10 and at a sufficient distance, is formed a groove into which is fitted a snap ring 17. While the groove and snap ring retention arrangement is preferred, any other means of retaining the rod and weight in the well can be used, such as for example, a retainer pin fitted through the portion of the rod projecting beyond the block, a retainer collar machined on the projecting rod portion, and the like. A sample carrier loaded into the well pushes the rod and weight up within the well, the rod being slidingly carried in opening 13, while during unloading, the weight exerts a force down on the carrier, helping to expel it from the well, the snap ring retaining the rod and weight within the well. While this arrangement is preferred, any other means may be employed to help expel carriers from the wells, as for example, spirally wound compression springs attached to the bottom of the wells.

The means for temperature control of the incubator can be effectuated, as shown in FIG. 4, by attaching either heating elements or thermoelectrical devices 18 and 19 to the block at convenient attachment sites. A thermistor 20 is used in order to sense and regulate the temperature of the incubator. While heating is normally used in incubation, if thermoelectrical devices are used, reversing their polarity will effectuate cooling of the incubator. Additonally, provisions can be made for the direct reading of the incubator temperature, as by a thermometer 21 inserted into the body of the incubator, as shown in FIG. 5.

The position of the incubator block 10 is shown in FIG. 4. The block 10 slidingly rests upon a pair of insulating plates 22 and 23, whose relationships to one another and the block can be seen in FIG. 4. These plates, made of a material which is non-conductive of and resistant to heat or cold, not only form the surface upon which block 10 both rests and is slidingly moved, but also form an insulating surface to prevent heat loss from the wells 11. As can be seen in FIG. 5, both plates are set within frame members 24 and 25, plate 22 being between and fixedly mounted to the frame members 24 and 25, and when block 10 is in its normal position of rest, it rests completely upon plate 22, as shown in FIG. 4. Plate 23, however, is slidably mounted within frame members 24 and 25 and is carried on rollers 26 which are attached to frame members 24 and 25. These rollers help overcome friction forces when block 10 and plate 23 are longitudinally slid to the right, as viewed in FIG. 4, during the incubator loading or unloading sequence to be immediately described.

During the position of rest, plates 22 and 23, lying in the same plane, abut upon each other, as shown in FIG. 4. In such a state of abutment, the plates are "closed" and form a continuous surface upon which block 10 can be moved longitudinally. When, however, it is desired to load sample carriers into the block 10 or unload them therefrom, block 10, as will be described hereinafter, is slidingly shifted from its position of rest on plate 22. By so moving, the foot 27, tensioned outwardly and downwardly by spring 28 and carried in plate 29, which is attached to the front face 10a of the block 10, comes into contact with the top surface of plate 23 and, by means of frictional drag, drives plate 23 to the right, as viewed in FIG. 4. The progress of plate 23 to the right is checked by stop 30, which is the end frame member to frame members 24 and 25. This movement and the frictional driving of plate 23 to the right separates the plates by a given increment and positions a row of wells over the transverse space thus created. Any further shifting of block 10 to the right with the plates separated will place successive rows of wells over the transverse space, while plate 23 remains against stop 30. Thus, the frictional drag of foot 27 on plate 23 is overcome and the block is merely slidingly shifted to the right. Closing the plates is merely the reverse of separating. Frictional drag of the foot 27 on plate 23, while block 10 is being shifted to the left, causes plate 23 to once again abut against plate 22, with block 10 merely being slidingly shifted to the left once plate closure is attained. Plates 22 and 23 are preferably bevelled 31 and 32, so that sample carriers loaded into wells 11 will be gradually completely nested into the wells by the passage of their lower portions over the bevelled surfaces.

The incremental, bidirectional shifting of block 10 over insulating plates 22 and 23 is carried out by means of features shown in FIG. 1 and FIG. 7. Block 10, as shown in FIG. 1, is provided with a row of blind bores 33, formed along the length of the block, parallel with and adjacent a lengthwise row of wells 11, each bore being in alignment with the widthwise rows of wells.

The blind bores 33 are so spaced that shifting of the block by one increment will always center a widthwise row of wells over the transverse space created by the separation of plates 22 and 23. The blind bores of the block cooperate with the indexer arrangement shown in the detailed diagram in FIG. 7. Vertically fixed pin 34 is attached to one end of a linkage means such as movable plate 35. Plate 35 is eccentrically linked to rotable discs 36 and 37, by pins 38 and 39, respectively. Discs 36 and 37 are such as to be synchronously driven by a third disc 40 by any convenient drive arrangement, such as friction drive, gears and the like. Disc 40 is connected to any suitable bidirectional drive means, such as that shown in FIG. 4 — a motor 41 driving gear 42 which drives chain 43 which in turn drives disc 40. While a preferred embodiment is shown, any suitable drive means which will bidirectly drive discs 36 and 37 can be used. When activated, rotational motion imparted to discs 36 and 37 imparts a translational motion to plate 35 whereby vertical pin 34, having a truncated tip that during the pin's position of rest is always partially engaged in a blind bore 33, is given a cyclic path of movement, one cycle of rotation of discs 36 and 37 imparting one cycle of rotation to vertical pin 34. During a portion of its cyclical course, pin 34 slidably mates with a blind bore 33 and "indexes" or pushes the block 10 in either direction by such an increment as to shift the next row of wells over the space created by the separated plates 22 and 23 and then disengages toward the end of its cycle to trip switch 44 so as to deactivate motor 41 and thereby to come to its rest position of partial engagement with a blind bore. Thus, each cycle of the pin indexes the block so as to shift it in either direction by the increment of one row of wells.

In order for the incubation apparatus to function automatically, there must be provided a means for automatically and continually transporting sample carriers in their holders to and from the incubator, as well as a means for loading and unloading the incubator. A preferred transportation system is a "railway" system which may comprise a main linear guide rail along which a holder having a row of sample carriers supported therein is adapted to be moved longitudinally stepwise to transport the carriers in the holders to a given station or point of operation. The holder is provided with a guide structure along its base by which the holder may be moved longitudinally along the track or rail. Further, the guide structure is so constructed as to allow the transverse motion of the holder laterally from one such track onto another "branch" rail or track of similar construction, but extending perpendicularly to the first track. Means is also provided for moving the holder along the main rail. In FIGS. 4, 5 and 6, 45 and 46 are sections of such a railway system which communicate with the incubation apparatus of this invention. Thus, the railway sections 45 and 46 fixed to a platform 47 are used to automatically transport sample carrier holders 48 continually to and from the incubator in such a way that the incubation station is only one stopping point for the samples which are to be routed from and to other stations. Once a holder with sample carriers is transported to and disposed beneath the incubator block 10, the sample carriers must be loaded into the block (or after incubation, unloaded from the block). Loading and unloading is preferably effectuated by the mechanism shown in FIGS. 4 and 5; however, any other means which will load and unload the incubator block is within the scope of the invention.

In the preferred loading mechanism shown in the figures, frame members 24 and 25 have passageways 49 which correspond to and are in alignment with the transverse space which is created by the movement of plate 23. When it is desired to load or unload block 10, the sample carrier holder 48 with sample carriers 50 is automatically transported on the railway, through frame passageway 49 into such position as to be disposed beneath the transverse space created by movement of plate 23. During this emplacement of the holder, the latter trips a switch 51, which activates motor means 41, whereby block 10, which is in its rest position, is indexed by one increment to the right, by which motion plate 23 is slid to the right, as shown in FIG. 4, creating the transverse space and at the same time positioning a row of wells over the space. Holder 48, by example, can have openings 52 in its base, the openings not being sufficiently large as to allow the sample carriers to pass through, yet large enough to allow "fingers" or rods 53 to pass through them. As the holder is disposed beneath the opening, it trips a switch 54, in FIG. 5, which activates drive motor 55. Drive motor 55 has a shaft 56, which carries a flange 57, to which is attached arm 58 with an offset 59 at one end, while the other end is linked to pin 60, which is fixedly carried by a plate 61. The latter fixedly carries another pin 62, which is linked to carrier frame 63, this frame being slidingly mounted on frame rod member 64 and fixedly carrying fingers 53. Two switches 65 and 66 are attached to platform 67 and are so positioned as to be trippable by one end of arm 58 and the offset 59 thereof, respectively. Fingers 53 pass through openings created in platform 47. Thus, when switch 54 is tripped, it activates drive motor 55, which sets into motion the arm and linkage arrangement, which in turn causes carrier frame 63 to be moved in an upward direction, thereby also lifting fingers 53 through the openings in platform 47. The fingers 53 also pass through openings 52 in the holder 48, these openings being in alignment with those in the platform 47 so as to contact the bases of sample carriers 50 and lift them into the row of wells 11 already disposed over the holder and carriers. As the fingers 53 reach their limit of upward motion, offset 59 of arm 58 trips switch 66.

The tripping of switch 66 deactivates drive motor 55 leaving fingers 53 supporting the sample carriers in the row of wells, and also activates motor 41 thereby causing the indexer to shift block 10 to the right by one row of wells so as to position the next row of wells over the space. As the indexer completes its cycle, it trips switch 44 which deactivates motor 41 and reactivates drive motor 55 so that the lifting mechanism completes its cycle of operation, whereby fingers 53 and carrier frame 63 are returned down to their initial position. As the cycle of operation nears its completion, arm 58 trips switch 65, thereby deactivating drive motor 55 and simultaneously activating motor means 68 of the loading/unloading area clearing mechanism.

The clearing of the loading/unloading area is effectuated by the mechanism shown in FIGS. 4 and 6. The drive motor means 68, activated by the tripping of switch 65, carries a shaft 69 on which is mounted disc 70. A connecting rod 71 is eccentrically mounted on disc 70 by linkage to pin 72 fixedly mounted in the face of disc 70. This connecting rod 71 is connected to pushing rod 73 by means of a yoke and tongue linkage 74 and is carried through support blocks 75 and 76. Thus, activation of motor means 68 causes pushing rod 73 to be driven to the left, pushing an empty holder to the left onto yet another railway section 77 attached to platform 47. The holders, as they are emptied, are pushed onto railway section 77 and stored beneath plate 22, while immediately allowing the next full holder to be interposed beneath block 10. The empty holders are forced by the action of pushing rod 73 against carriage 78, which is slidably mounted in platform 47. This carriage 78 is tensioned in the direction towards support block 75 by a negatory spring 79. The spring causes carriage 78 to exert a force to the right, as shown in FIG. 4, and against any holders interposed between it and support block 75. Thus, all successive holders after the first, during loading or unloading, are held between support block 75, and empty holders being forced against the loading or unloading holder by the effect of negatory spring 79. The operation of pushing rod 73 to push empty holders out of the way of incoming full holders is reciprocal in nature. Thus, each activation of the pusher results in the empty holder being pushed out of the way, with pushing rod 73 returning to its normal position of rest and tripping switch 80 so as to deactivate drive motor means 68.

The block is incrementally shifted to the right, as shown in FIG. 4, by the indexer so long as there is a holder depressing switch 51. Once the last holder is cleared out of the loading/unloading area by pushing rod 73, switch 51 is released, whereby bidirectional motor means 41 is activated so as to index the block 10 back towards its rest position. Once the indexer is activated into shifting the block back, it will continue to do so until block 10 achieves its rest position, thereby tripping switch 81 which deactivates the indexer. During its return to its rest position, block 10 also moves plate 23 so as to close the transverse space. The incubator starts incubating a set of samples as soon as they are loaded. Thus, by returning to its position of rest, the samples can be unloaded in the exact same sequence as they were loaded, with already incubated samples being unloaded first. In unloading, the empty holders stored under plate 22 are disposed in turn under the space to receive the incubated samples and then exit through the passageway in frame member 25, to be sent automatically to the next station or operation in the analytical procedure.

While the various operations that are to be performed in the loading and unloading of the incubator have been described and illustrated as occurring by the proper sequencing of various electrical switches in the apparatus, it is possible and it is within the scope of the invention that these functions could be controlled by a logic means or device properly programmed so as to perform all the operations in properly timed sequential order.

During actual use of the incubation apparatus in an analytical system, it is desirable to shield it with insulating material to keep heating or cooling loss at a minimum. Thus, it is possible to sheath the incubator block with an insulating material, such as for example, foamed polystyrene. However, any insulating material can be used.

Thus, an incubation apparatus has been provided which allows sample carriers to be automatically loaded into, incubated in and unloaded from a heat block incubator in a simple and efficient manner, and which, by automatic sequential loading and unloading, not only obviates manual loading and unloading but also overcomes the problem of accidental errors of identification that are likely in manual operations.

Although the present invention has been described in detail in several illustrative embodiments, it is to be understood that the novelty of the invention is not limited to specific embodiments illustrated and described, but is defined only by the scope of the appended claims.

We claim:

1. An incubation apparatus for use in automated biochemical analyzer systems, which comprises
    a block of thermoconductive material having means for temperature control attached thereto and a plurality of rows of regularly spaced wells, said wells extending into the block from a bottom surface of the block and having openings facing downward;
    a pair of flat plates of insulating material, said plates lying in the same plane, each with an edge in mutual abutment, one plate being fixed and the other longitudinally slidable a given incremental distance in a direction away from the point of abutment, with the block with well openings facing downward being slidably carried upon said pair of insulating plates; and
    means for lifting into a row of wells a set of sample carriers from a carrier holder disposed directly beneath the block and insulating plates and in alignment with a row of wells in the block exposed to the carrier holder by a transverse space created by incrementally sliding the slidable plate, and for lowering a set of sample carriers from a row of wells into a carrier holder disposed directly beneath and in alignment with the row of wells.

2. The apparatus of claim 1, where the well openings are flared, and each well extremity has means for aiding in expulsion of sample carriers from the wells during unloading thereof.

3. The apparatus of claim 2, where the means aiding in expulsion of sample carriers from the wells comprises a rod, at one end of which is attached a weight, said rod extending through an opening in each well extremity, said opening passing completely through the block, and said weight being contained within the well and the rod being slidingly carried in the opening and projecting beyond the block, said projecting rod portion being provided with a means for retaining the rod and weight within the well.

4. The apparatus of claim 1, where the apparatus further comprises means for incrementally and bidirectionally shifting the block over the insulating plates, whereby all or some of the rows of wells in the block can be loaded or unloaded in sequential order.

5. The apparatus of claim 1, where the apparatus further comprises means for sensing and regulating the temperature of the block.

6. The apparatus of claim 4, wherein the means for incrementally shifting the block comprises a row of blind bores formed adjacent and parallel with a lengthwise row of wells, each bore being in alignment with each widthwise row of wells; and a pin slidably matable with the blind bores and fixedly mounted in a vertical position to one end of a linkage means, such that translational motion of the linkage imparts to the pin a cyclic path whereby the pin mates fully with a blind bore, indexes the block for a given incremental distance and then disengages from the blind bore, thereby completing one cycle, each cycle shifting the block in a given direction by an incremental distance.

7. The apparatus of claim 1, where the thermoconductive block material is aluminum.

8. The apparatus of claim 1, further comprising means for clearing empty holders from beneath a row of wells to a position of storage beneath the fixed insulating plate.

* * * * *